US005760273A

United States Patent [19]

Inaba et al.

[11] Patent Number: 5,760,273
[45] Date of Patent: Jun. 2, 1998

[54] PROCESS FOR PRODUCING UNSYMMETRICAL CHAIN CARBONIC ACID ESTER

[75] Inventors: Masashi Inaba; Katsuaki Hasegawa, both of Mie; Noriko Shimizu, Kanagawa; Yuji Ohgomori, Ibaraki; Masayuki Honda; Takamichi Suzuki, both of Mie, all of Japan

[73] Assignee: Mitsubishi Chemical Corporation, Tokyo, Japan

[21] Appl. No.: 733,871

[22] Filed: Oct. 18, 1996

[30] Foreign Application Priority Data

Oct. 25, 1995 [JP] Japan ................................. 7-278120
Jun. 11, 1996 [JP] Japan ................................. 8-148880

[51] Int. Cl.[6] ........................................... C07C 69/96
[52] U.S. Cl. ........................ 558/277; 502/302; 502/327; 502/355
[58] Field of Search ................. 558/277; 502/302, 502/327, 355

[56] References Cited

U.S. PATENT DOCUMENTS 3,642,858  2/1972  Frevel .
3,803,201  4/1974  Gilpin .
5,118,818  6/1992  Delledonne ........................... 549/230
5,206,408  4/1993  Liotta, Jr. ............................. 558/277
5,322,958  6/1994  Dreoni .................................. 558/277
5,430,170  7/1995  Urano .................................. 558/277
5,436,362  7/1995  Kondoh ................................ 558/277
5,498,743  3/1996  Shih .................................... 558/277

OTHER PUBLICATIONS

CA:122: 213631 Abst. JP0701811 Jan. 13, 1995 Hasegawa "Prep of asymmetric dialkyl carbonates".

Primary Examiner—C. Warren Ivy
Assistant Examiner—Jean F. Vollano
Attorney, Agent, or Firm—Dilworth & Barrese

[57] ABSTRACT

A process for producing an unsymmetrical chain carbonic acid ester is described, which comprises reacting a first symmetrical chain carbonic acid ester with a second symmetrical chain carbonic acid ester or a monohydric alcohol in the presence of a catalyst comprising as an active catalyst component an oxide of at least one element selected from the Group IIIB elements of the periodic table.

20 Claims, No Drawings

5,760,273

PROCESS FOR PRODUCING UNSYMMETRICAL CHAIN CARBONIC ACID ESTER

FIELD OF THE INVENTION

The present invention relates to a process for producing an unsymmetrical chain carbonic acid ester.

More particularly, this invention relates to a process for producing in high yield an unsymmetrical chain carbonic acid ester by (i) reacting two symmetrical chain carbonic acid esters by disproportionation or (ii) reacting a symmetrical carbonic acid ester with an alcohol, using a catalyst comprising an oxide of a Group IIIB element.

Unsymmetrical chain carbonic acid esters are useful compounds as solvents for electrolytic solutions for lithium secondary batteries, solvents for resins and of coating compositions, etc., alkylating agents, or starting materials for carbamate syntheses.

BACKGROUND OF THE INVENTION

Since carbonic acid is a dibasic weak acid, monoesters and diesters of the acid exist. The diesters include symmetrical chain carbonic acid esters in which the two alkyl groups are the same and unsymmetrical chain carbonic acid esters in which the two alkyl groups are different. The prior art processes proposed so far for the industrial production of chain carbonic acid esters include the reaction of phosgene with alcohols and the reaction of alcohols with carbon monoxide and oxygen in the presence of a catalyst. However, since phosgene is a toxic gas, it is undesirable to employ the process in which phosgene is used.

On the other hand, the process in which an alcohol is reacted with carbon monoxide and oxygen in the presence of a catalyst is intended to produce a symmetrical chain carbonic acid ester and is unsuitable for the production of unsymmetrical chain carbonic acid esters, which the present invention is intended to produce.

Consequently, for producing an unsymmetrical chain carbonic acid ester, use has hitherto been made of either a process in which a symmetrical chain carbonic acid ester is subjected to transesterification with an alcohol having a different alkyl group or a process in which two symmetrical chain carbonic acid esters are subjected to disproportionation and the resulting unsymmetrical chain carbonic acid ester as the target compound is separated from the equilibrium mixture.

An example of the former process is proposed in JP-A-6-166660, in which a monohydric alcohol is reacted with a symmetrical chain carbonic acid ester by transesterification using an alkali metal carbonate as a catalyst to produce an unsymmetrical chain carbonic acid ester. (The term "JP-A" as used herein means an "unexamined published Japanese patent application.") This method, however, has the following drawbacks. Since the alkali metal carbonate used as a catalyst for the above transesterification is poorly soluble in alcohols, i.e., not completely insoluble in alcohols, it is necessary to remove the alkali metal carbonate-present in the reaction mixture in a slight amount after the reaction so as to prevent the carbonate from causing the reverse reaction in the subsequent separation step. This removal of the alkali metal carbonate is somewhat troublesome and time-consuming. Further, since alkali metal carbonates generally are readily soluble in water, the proposed method has the problem that accidental contact of the catalyst with water results in serious trouble in the reaction process.

An example of the latter process is proposed in JP-A-7-10811, in which a mixture of three dialkyl carbonates including an unsymmetrical chain carbonic acid ester is obtained using a basic catalyst, e.g., an alkali metal alcoholate, and the unsymmetrical chain carbonic acid ester is isolated from the mixture by distillation. However, strong bases such as alkali metal alkoxides have drawbacks in that the handling and storage thereof are difficult because they are injurious to the human body upon contact therewith, and because they are hygroscopic and are degraded by water. In addition, such a homogeneous catalyst system is industrially disadvantageous in that the removal of the catalyst after the reaction necessitates troublesome steps including extraction with water, and that the water added for the post-treatment should be removed and this requires much labor. Therefore, the latter process is not an industrially advantageous method.

As described above, the methods proposed in the references cited above are still insufficient from an industrial standpoint.

SUMMARY OF THE INVENTION

An object of the present invention is to provide a catalyst which is useful in a heterogeneous catalyst system for the catalytic disproportionation of two symmetrical chain carbonic acid esters to obtain an equilibrium mixture containing an unsymmetrical chain carbonic acid ester as the target compound, and which is stable, highly active, and insoluble in the reaction mixture from which the target compound is isolated.

Another object of the present invention is to provide a simple process for producing an unsymmetrical chain carbonic acid ester with high selectivity.

Still another object of the present invention is to provide a process for producing an unsymmetrical chain carbonic acid ester in high yield by reacting a symmetrical carbonic acid ester with an alcohol using a specific catalyst.

The present invention provides, according to a first embodiment thereof, a process for producing an unsymmetrical chain carbonic acid ester by reacting two symmetrical chain carbonic acid esters by disproportionation in the presence of a catalyst comprising as an active catalyst component an oxide of at least one element selected from the Group IIIB elements of the periodic table.

The present invention further provides, according to a second embodiment thereof, a process for producing an unsymmetrical chain carbonic acid ester by reacting a carbonic acid ester with a monohydric alcohol by transesterification in the presence of a catalyst comprising as an active catalyst component an oxide of at least one element selected from the Group IIIB elements of the periodic table.

DETAILED DESCRIPTION OF THE INVENTION

The process of the first embodiment of the present invention is now explained in detail. In the presence of a catalyst comprising an oxide of at least one Group IIIB element, the disproportionation reaction of two symmetrical chain carbonic acid esters proceeds according to the following reaction scheme (1) to yield an unsymmetrical chain carbonic acid ester as the target compound.

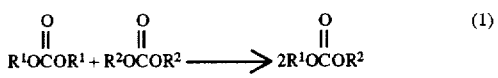

(1)

In reaction scheme (1), $R^1$ and $R^2$ represent different alkyl groups which may be linear, branched, or cyclic.

The alkyl groups are not particularly limited in the number of carbon atoms thereof. However, they each have generally from 1 to 12, preferably from 1 to 6, carbon atoms. Examples of the alkyl groups include linear alkyl groups such as methyl, ethyl, propyl, butyl, pentyl, hexyl, heptyl, octyl, and dodecyl; branched alkyl groups such as isopropyl, isobutyl, sec-butyl, tert-butyl, isoamyl, tert-amyl, neopentyl, isohexyl, sec-hexyl, and tert-hexyl; and cyclic alkyl groups such as cyclopropyl, cyclobutyl, cyclopentyl, cyclohexyl, cycloheptyl, cyclooctyl, cyclododecyl, and norbornyl.

Specific examples of the symmetrical chain carbonic acid esters used as starting materials include dimethyl carbonate (DMC), diethyl carbonate (DEC), dipropyl carbonate, dibutyl carbonate, and dicyclohexyl carbonate.

Specific examples of the unsymmetrical chain carbonic acid ester as the target compound include ethyl methyl carbonate (EMC), methyl propyl carbonate, ethyl propyl carbonate, butyl methyl carbonate, butyl ethyl carbonate, and butyl propyl carbonate.

What starting materials which should be used are determined by the target compound. For example, in the case of producing EMC as the target compound, DMC and DEC are used as starting materials.

The catalyst used in the present invention comprises an oxide of at least one Group IIIB element as an active catalyst component. This active catalyst component is not limited to one consisting only of an oxide of at least one Group IIIB element, and may further contain compounds of elements other than the Group IIIB elements, e.g. cobalt. In particular, an active catalyst component containing one or more Group IIIB elements and cobalt is superior in the long-term retention of activity. Examples of the Group IIIB elements include Sc, Y, the lanthanide series elements, i.e., La, Ce, Pr, Nd, Pm, Sm, Eu, Gd, Tb, Dy, Ho, Er, Tm, Yb, and Lu, and actinide series elements such as Ac, Th, Pa, and U. These elements may be used alone or in combinations of two or more thereof. Although it is essential that the catalyst for use in the present invention comprise an oxide of at least one of such Group IIIB elements, the oxide is not particularly limited as to whether the Group IIIB elements have an oxidation number of 3 or higher or have two or more oxidation numbers. Preferred oxides of these Group IIIB elements are yttrium oxide, samarium oxide, and oxides of mixtures of rare earth elements, because these oxides are easy to industrially utilize. These Group IIIB element oxides can be produced, for example, from the oxalates, acetates, nitrates, hydroxides, carbonates, or similar compounds of Group IIIB elements by baking the same in air. Alternatively, commercially available oxides of Group IIIB elements can also be utilized.

The oxide used as a catalyst preferably is porous and has a large specific surface area because this type of oxide can have high catalytic activity. The specific surface area of the oxide is usually from 5 to 500 $m^2/g$, preferably from 10 to 300 $m^2/g$. Oxides having a specific surface area smaller than 5 $m^2/g$ are undesirable in that sufficient catalytic activity cannot be obtained. Oxides having a specific surface area exceeding 500 $m^2/g$ are undesirable in that the catalyst has reduced strength and impaired durability.

Before being used as a catalyst, these oxides are preferably activated by heating in a stream of an inert gas, e.g., nitrogen, to remove adsorbates present on the oxide surface, e.g., carbon dioxide and water. The temperature for this heat treatment is from 100° to 1,000° C., preferably from 200° to 800° C. Temperatures lower than 100° C. are undesirable in that the desorption of adsorbates is insufficient. Temperatures exceeding 1,000° C. are undesirable in that not only the heat treatment is costly, but the oxides partly fuse, resulting in a reduced surface area. Although the time period for the treatment for activation varies depending on the amount of adsorbates and the temperature for the treatment and is hence not particularly limited, it is usually from 1 to 10 hours.

The catalyst is not particularly limited in its form. It is however desirable that the catalyst be in a form which facilitates the flow of reactants through the catalyst and catalyst separation after the reaction. Although the catalyst may be in the form of fine particles of about 100 μm, it is preferably in the form of pellets molded by a general technique, e.g., granulation or punching.

An appropriate binder may be used in the catalyst preparation for the purpose of bonding the solid oxide particles of the catalyst to enhance the mechanical strength of the catalyst. The binder may be an inorganic or organic substance which does not adversely influence the activity of the catalyst or exhibits some degree of catalytic activity in the reaction. Examples of the binder include silica sol, alumina sol, zirconia sol, and organic polymers.

An appropriate support may be used in the catalyst preparation for the purpose of providing a catalyst in which particles of the Group IIIB element oxide are dispersed on the support surface to attain a large surface area or providing a catalyst which has enhanced mechanical strength. The support is not particularly limited as long as it neither inhibits the reaction nor adversely influences the catalytic activity. A support which exhibits some degree of catalytic activity may be used. Examples of the support for use in the present invention include inorganic supports such as silica, alumina, zirconia, titania, silica-alumina, zirconia-titania, and silica-zirconia, kaolinite minerals such as kaolinite, dickite, and halloysite, smectite minerals such as montmorillonites and beidellite, mica group minerals such as common mica, palagonite, phlogopite, and biotite, and clay minerals such as hydrotalcites and talc.

The molar ratio between the two symmetrical chain carbonic acid esters used as starting materials is not particularly limited. However, it is usually preferred to use the starting materials in a substantially equimolar amount, from the standpoint of heightening the yield of the target unsymmetrical chain carbonic acid ester. As a matter of course, an excess of either of the starting materials may be used to conduct the reaction. The molar ratio between the reactants is preferably selected from the range of from 1:1 to 1:20.

Reaction temperature is not particularly limited. However, the reaction is usually conducted at from 0° to 300° C., preferably from 50° to 200° C., in an inert gas atmosphere, e.g., nitrogen. Too low reaction temperatures are undesirable in that reduced reaction rates result, while too high reaction temperatures are undesirable in that side reactions are more apt to occur. Reaction pressure is not particularly limited. Although the reaction can be conducted at a pressure of from 0.1 to 100 kg/cm²·G, it is usually conducted at a pressure of from 0 to 50 kg/cm²·G, preferably from 0 to 10 kg/cm²·G.

The catalyzed disproportionation reaction of symmetrical chain carbonic acid esters according to the present invention may be carried out by a batch process or a flow process without particular limitations. However, a flow process is economically preferred for industrial production, because the starting materials can be continuously treated in large quantities and the catalyst can be used repeatedly over an extended period of time.

In the case where the reaction is conducted by a batch process, the catalyst is used in an amount of from 0.01 to 30% by weight, preferably from 0.1 to 15% by weight, based on the amount of the starting materials. The catalyst and starting materials according to the present invention are introduced into a batch reactor in predetermined amounts, and the starting materials are reacted by disproportionation with stirring at a predetermined temperature, whereby a reaction mixture containing the target unsymmetrical chain carbonic acid ester is obtained. Although the reaction time varies depending on the reaction temperature and the amount of the catalyst used, it is generally from 0.1 to 100 hours, preferably from 1 to 10 hours.

In the case where the reaction is conducted by a flow process, the process may be any of the fixed bed, fluidized bed, and stirring vessel types. In this process, the reactants may be passed through the reactor at a liquid hourly space velocity (LHSV) based on the catalyst of from 0.05 to 50 $hr^{-1}$, preferably from 0.1 to 10 $hr^{-1}$.

In the process of the present invention for producing an unsymmetrical chain carbonic acid ester, the reaction proceeds in a liquid phase. Since the two symmetrical chain carbonic acid esters themselves used as starting materials function as a solvent in this reaction, there is no need of using a solvent. Although nonuse of a solvent is preferred from the standpoint of the easiness of post-treatment, a solvent may be used as long as it neither reacts with any of the starting materials and the reaction product nor interferes with separation after the reaction. Examples of such solvents include aromatic hydrocarbons, saturated hydrocarbons, unsaturated hydrocarbons, ethers, and amides.

After the reaction, the two symmetrical chain carbonic acid esters used as starting materials and the unsymmetrical chain carbonic acid ester yielded as the reaction product can be separated from one another by any known distillation technique, e.g., atmospheric distillation, vacuum distillation, or pressure distillation. The reaction mixture may be distilled as is because of the absence of a catalyst dissolved therein, or the reaction mixture may be distilled after fine catalyst particles present therein in a slight amount are removed by filtration, etc. In this fractional distillation, the components effuse in the order of boiling point, i.e., one of the symmetrical chain carbonic acid esters used as starting materials effuses first and the unsymmetrical chain carbonic acid ester as the target compound effuses next, followed by the chain carbonic acid ester as the other starting material. Consequently, the target compound can be obtained as the second distillation fraction with a desired purity. Of the starting materials used, the symmetrical chain carbonic acid ester having a higher boiling point may be effused out, or may be left in the distilling tank and recycled to reaction. In the process of the present invention for producing an unsymmetrical chain carbonic acid ester, since substantially no reaction products except the unsymmetrical chain carbonic acid ester are yielded from the symmetrical chain carbonic acid esters used as starting materials, the target reaction product can be obtained with high selectivity. In addition, the starting materials recovered can be reused.

The process of a second embodiment of the present invention is now explained below in detail.

The transesterification reaction of a carbonic acid ester with a monohydric alcohol proceeds in the following step (scheme (1)) to yield a chain carbonic acid ester as the target compound and the corresponding alcohol.

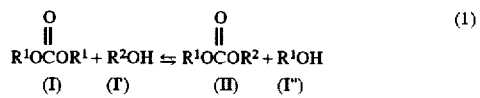

But, occasionally happens the following by-product reaction.

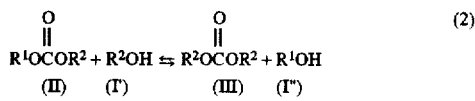

In the above schemes (1) and (2), $R^1$ and $R^2$ represent different alkyl groups which may be linear, branched, or cyclic.

The alkyl groups are not particularly limited in the number of carbon atoms thereof. However, they each have generally from 1 to 12, preferably from 1 to 6, carbon atoms. Examples of the alkyl groups include linear alkyl groups such as methyl, ethyl, propyl, butyl, pentyl, hexyl, heptyl, octyl, and dodecyl; branched alkyl groups such as isopropyl, isobutyl, sec-butyl, tert-butyl, isoamyl, tert-amyl, neopentyl, isohexyl, sec-hexyl, and tert-hexyl; and cyclic alkyl groups such as cyclopropyl, cyclobutyl, cyclopentyl, cyclohexyl, cycloheptyl, cyclooctyl, cyclododecyl, and norbornyl.

In order for the transesterification shown by the reaction scheme (1) above to proceed speedily and efficiently, a transesterification catalyst is used which comprises an oxide of at least one element selected from the Group IIIB elements described above.

The symmetrical chain carbonic acid ester represented by formula (I) can be selected from the symmetrical chain carbonic acid esters enumerated hereinabove. Of those, dimethyl carbonate or diethyl carbonate is advantageous in that they are easily available.

The alcohol is a monohydric alcohol represented by formula (I) shown above. The alkyl group $R^2$ in the formula is different from $R^1$ of the carbonic acid ester represented by formula (I).

Specific examples of the monohydric alcohol include methyl alcohol, ethyl alcohol, n-propyl alcohol, isopropyl alcohol, n-butyl alcohol, isobutyl alcohol, t-butyl alcohol, pentyl alcohol, hexyl alcohol, octyl alcohol, 2-ethylhexyl alcohol, decyl alcohol, dodecyl alcohol, tetradecyl alcohol, hexadecyl alcohol, octadecyl alcohol, and cyclohexyl alcohol. Desirable of these are the aliphatic alcohols having 1 to 6 carbon atoms. From the standpoint of reactivity, methanol and ethanol are especially preferred.

The transesterification reaction proceeds in a liquid phase. Since the starting materials themselves, i.e., a carbonic acid ester and an alcohol, function as a solvent, there is no need of using a solvent. Although omission of a solvent is preferred from the standpoint of the easiness of post-treatment, a solvent may be used as long as it does not react with any of the starting materials or the reaction products. Examples of such solvents include aromatic hydrocarbons, saturated hydrocarbons, unsaturated hydrocarbons, ethers, and amides. These solvents may be used alone or as a mixture thereof.

Methods for carrying out the transesterification reaction according to the present invention are now explained. The proportion between the chain carbonic acid esters yielded as reaction products varies depending on the molar ratio between the carbonic acid ester and alcohol fed as starting materials. Consequently, by suitably selecting the molar ratio between the starting materials fed, the target chain carbonic acid ester (II) can be obtained in an increased proportion. Although the molar ratio between the carbonic acid ester and the alcohol both used as starting materials is not particularly limited, the molar ratio of the alcohol to the starting carbonic acid ester is usually from 0.1 to 50, preferably from 0.5 to 5. Too large proportions of the alcohol to the carbonic acid ester result in increased amounts of the alcohol to be recovered, while too small proportions thereof result in reduced conversions of the starting carbonic acid ester.

In accordance with the practice of the present invention, the transesterification reaction of a monohydric alcohol with a carbonic acid ester may be carried out by a batch process or a flow process without particular limitations.

In the case where the reaction is conducted by a batch process, the catalyst is used in an amount of from 0.1 to 30% by weight, preferably from 1 to 15% by weight, based on the amount of the starting materials. The catalyst and the starting materials are introduced into a batch reactor in predetermined amounts, and the starting materials are reacted by transesterification with stirring at a predetermined temperature, whereby a reaction mixture containing the target chain carbonate is obtained. Although the reaction time varies depending on the reaction temperature and the amount of the catalyst used, it is generally from 0.1 to 100 hours, preferably from 1 to 40 hours.

In the case where the reaction is conducted by a flow process, the process may be any of the fixed bed, fluidized bed, and stirring vessel types. In this process, the reactants may be passed through the reactor at a liquid hourly space velocity (LHSV) based on the catalyst of from 0.05 to 50 $hr^{-1}$, preferably from 0.1 to 10 $hr^{-1}$.

Reaction temperature is not particularly limited. However, the reaction is usually conducted at from 0° to 300° C. in an inert gas atmosphere, e.g., nitrogen. From the standpoint of the easiness of reaction operations, a preferred temperature range is from 50° to 200° C. Reaction pressure is not particularly limited. Although the reaction can be conducted at a pressure of from a vacuum to 200 $kg/cm^2 \cdot G$, it is usually conducted at a pressure of from 0 to 60 $kg/cm^2 \cdot G$, preferably from 0 to 30 $kg/cm^2 \cdot G$.

After completion of the reaction, the reaction mixture can be filtered to remove fine catalyst particles. It should, however, be noted that there are cases where the reaction mixture contains a slight amount of a catalyst component dissolved therein depending on combinations of the catalyst and alcohol used. In this case, the catalyst can be removed by adding a solid acid substance such as, e.g., activated clay, silica gel, or an ion exchange resin to the reaction mixture, or by passing the reaction mixture through a column packed with the acid substance. Thus, catalyst removal can be accomplished without using water according to the present invention. Therefore, there is no need of conducting oil/water separation or water removal, which is a troublesome, time-consuming post-treatment.

After catalyst removal, the components of the reaction mixture, i.e., the carbonic acid ester used as a starting material, the carbonic acid esters yielded as reaction products, and alcohols, can be separated from one another by known techniques, e.g., atmospheric distillation, vacuum distillation, or pressure distillation. In this embodiment of the process of the present invention for producing a carbonic acid ester, since the reaction mixture resulting from the transesterification comprises the carbonic acid ester used as a starting material, the carbonic acid esters yielded as reaction products, and alcohols and does not contain any other reaction product, the target reaction product can be obtained with high selectivity. In addition, the starting materials recovered can be reused.

The present invention will now be explained below in detail by reference to Examples, but the invention should not be construed as being limited to these Examples.

CATALYST PRODUCTION EXAMPLE 1

An aqueous samarium nitrate solution was obtained by dissolving 400.0 g (0.9 mol) of samarium nitrate hexahydrate in 1,000 g of water. To this aqueous samarium nitrate solution was added 3,500 g of 12% aqueous ammonium bicarbonate solution with stirring to obtain a samarium hydroxide slurry. This slurry was filtered, and the solid taken out was sufficiently washed with pure water until the pH of the washings became a neutral value. Thus, hydrous samarium hydroxide was obtained. This samarium hydroxide was dried in air at 120° C. for 12 hours and then baked at 600° C. for 3 hours to obtain samarium oxide, which is referred to as catalyst (1).

CATALYST PRODUCTION EXAMPLE 2

The same procedure as in Catalyst Production Example 1 was carried out, except that 344.7 g (0.9 mol) of yttrium nitrate hexahydrate was used in place of 400 g of samarium nitrate hexahydrate. Thus, yttrium oxide was obtained, which is referred to as catalyst (2).

CATALYST PRODUCTION EXAMPLE 3

The same procedure as in Catalyst Production Example 1 was carried out, except that a mixture of 172.3 g (0.45 mol) of yttrium nitrate hexahydrate and 131.1 g (0.45 mol) of cobalt nitrate hexahydrate was used in place of 400 g of samarium nitrate hexahydrate. Thus, an yttrium/cobalt compound oxide was obtained. In this catalyst, the proportion of yttrium metal atoms to cobalt metal atoms was 1:1. This catalyst is referred to as catalyst (3).

CATALYST PRODUCTION EXAMPLE 4

An appropriate amount of pure water was added to the baked powder obtained in Catalyst Production Example 3 to obtain a slurry. The slurry was kneaded with heating to impart the consistency of plasticized clay thereto, and then formed by extrusion molding into cylindrical granules having a diameter of 3 mm. The cylindrical granules were dried at 120° C. overnight and then baked at 600° C. for 3 hours. This catalyst is referred to as catalyst (4).

CATALYST PRODUCTION EXAMPLE 5 (COMPARATIVE)

The same procedure as in Catalyst Production Example 1 was carried out, except that 261.9 g (0.9 mol) of cobalt nitrate hexahydrate was used in place of 400 g of samarium nitrate hexahydrate. Thus, cobalt oxide was obtained, which is referred to as catalyst (5).

EXAMPLE 1

Into a stainless-steel autoclave having a capacity of 1,000 ml and equipped with a stirrer were introduced a solution prepared by mixing 180.2 g (2.0 mol) of dimethyl carbonate (DMC) and 236.3 g (2.0 mol) of diethyl carbonate (DEC) (molar ratio, 1:1) and 1.75 g (0.005 mol) of catalyst (1). Subsequently, the atmosphere in the reactor was replaced with nitrogen to regulate the nitrogen pressure inside the reactor to 1 kg/cm2·G. Thereafter, the temperature of the contents was raised and then kept at 140° C. to react the carbonates for 4 hours in total. The reaction pressure increased to 2.8 kg/cm²·G during the temperature rising, which took 1 hour, subsequently increased-slightly during the progress of the reaction performed at a constant temperature of 140° C., and then increased to 3.1 kg/cm²·G at the time of completion of the reaction.

After completion of the reaction, the reaction mixture was analyzed by gas chromatography. As a result, the reaction mixture was found to be composed of 104.5 g (1.16 mol) of dimethyl carbonate, 174.6 g (1.68 mol) of ethyl methyl carbonate (EMC), and 137.5 g (1.16 mol) of diethyl carbonate and not to contain any other reaction product. The yield of ethyl methyl carbonate, which was the target compound, based on all carbonates used as starting materials was 42.1 mol %.

EXAMPLE 2

The same procedure as in Example 1 was carried out, except that 0.9 g (0.005 mol) of catalyst (3) was used in place of catalyst (1). The resulting reaction mixture was composed of 109.0 g (1.21 mol) of DMC, 157.2 g (1.51 mol) of EMC, and 148.8 g (1.26 mol) of DEC, and did not contain any other reaction product. The yield of EMC, which was the target compound, based on all carbonates used as starting materials was 37.8 mol %.

EXAMPLE 3

The same procedure as in Example 1 was carried out, except that 1.13 g (0.005 mol) of catalyst (2) was used in place of catalyst (1). The resulting reaction mixture was composed of 113.6 g (1.26 mol) of DMC, 150.9 g (1.45 mol) of EMC, and 153.5 g (1.3 mol) of DEC, and did not contain any other reaction product. The yield of EMC, which was the target compound, based on all carbonates used as starting materials was 36.3 mol %.

EXAMPLE 4

A jacketed tubular reactor having an inner diameter of 54.9 mm and a length of 90 cm was packed with 127 ml (80 g) of catalyst (4). A 1:1 (by mole) mixture of DMC and DEC as starting materials was fed to the reactor with a constant delivery pump, and the pressure inside the reactor was regulated to 9 kg/cm²·G with nitrogen. Thereafter, the temperature of the contents was raised to 140° C. to conduct a continuous reaction while passing the reactants at an LHSV of 2. At 170 hours after initiation of the reaction, the reaction mixture was taken out and analyzed by gas chromatography. As a result, the reaction mixture obtained was found to comprise 21.6 wt % of DMC, 49.5 wt % of EMC, and 28.5 wt % of DEC and not to contain any other reaction product. The yield of EMC, which was the target compound, based on all carbonates used as starting materials was 49.5 mol %.

Using a distilling column in which the number of theoretical plates was 40, 1,800 g of the foregoing reaction mixture was distilled at ordinary pressure in a reflux ratio of 10. As a result, 534 g of an EMC fraction having a purity of 99.9% was obtained, which shows that 60 mol % of the EMC contained in the reaction mixture treated was recovered.

EXAMPLE 5

The reaction performed at 140° C. in Example 4 was continued under the same conditions, except that the LHSV was varied. The results obtained are shown in Table 1.

TABLE 1

| | | | |
|---|---|---|---|
| DMC/DEC molar ratio in starting materials | 1:1 | 1:1 | 1:1 |
| Passage of reaction time (hr) | 268 | 340 | 508 |
| LHSV (hr⁻¹) | 1 | 3 | 4 |
| Composition of reaction mixture (wt %) | | | |
| DMC | 21.4 | 22.4 | 23.5 |
| EMC | 49.9 | 48.0 | 45.6 |
| DEC | 28.3 | 29.4 | 30.8 |
| Yield of EMC (mol %) | 49.9 | 48.0 | 45.6 |

EXAMPLE 6

The reaction performed in Example 4 was continued at 140° C. under the same conditions, except that the dimethyl carbonate/diethyl carbonate molar ratio in the starting materials was changed. The results obtained are shown in Table 2.

TABLE 2

| | | |
|---|---|---|
| DMC/DEC molar ratio in starting materials | 1:1.5 | 1:2 |
| Passage of reaction time (hr) | 970 | 770 |
| LHSV (hr⁻¹) | 2 | 2 |
| Composition of reaction mixture (wt %) | | |
| DMC | 13.8 | 10.0 |
| EMC | 45.9 | 42.6 |
| DEC | 40.2 | 47.2 |
| Yield of EMC (mol %) | 47.1 | 44.5 |

EXAMPLE 7

The reaction performed in Example 4 was carried out under the same conditions, except that the temperature was changed to 120° C. The results obtained are shown in Table 3.

TABLE 3

| | | | |
|---|---|---|---|
| DMC/DEC molar ratio in starting materials | 1:1 | 1:1 | 1:1 |
| Passage of reaction time (hr) | 648 | 580 | 628 |
| LHSV (hr⁻¹) | 1 | 2 | 3 |
| Composition of reaction mixture (wt %) | | | |
| DMC | 22.4 | 24.5 | 26.4 |
| EMC | 46.9 | 42.8 | 37.8 |
| DEC | 30.6 | 32.7 | 35.7 |
| Yield of EMC (mol %) | 46.9 | 42.8 | 37.8 |

COMPARATIVE EXAMPLE 1

The same procedure as in Example 4 was carried out, except that 1.39 g (0.01 mol) of potassium carbonate was used as a catalyst in place of catalyst (4). The resulting reaction mixture was composed of 180.1 g (2.0 mol) of DMC, 0.1 g (0.001 mol) of EMC, and 228.1 g (2.0 mol) of DEC, and did not contain any other reaction product. The yield of EMC, which was the target compound, based on all carbonates used as starting materials was 0.05 mol %.

EXAMPLE 8

To a solution prepared by mixing 461 g (10 mol) of ethyl alcohol and 901 g (10 mol) of dimethyl carbonate (molar ratio, 1:1) was added 36.0 g (0.1 mol) of catalyst (1). This mixture was heated for 30 hours by immersion in a 100° C. oil bath. After the reaction, the resulting reaction mixture was analyzed by gas chromatography. As a result, the reaction mixture was found to be composed of 186 g (5.8 mol) of methyl alcohol, 194 g (4.2 mol) of ethyl alcohol, 441 g (4.9 mol) of dimethyl carbonate, 458 g (4.4 mol) of ethyl methyl carbonate, and 83 g (0.7 mol) of diethyl carbonate and not to contain any other reaction product.

After this reaction mixture was cooled to room temperature, the catalyst was removed by filtration. The filtrate was distilled at ordinary pressure using a distilling column in which the number of theoretical plates was 20, without subjecting the filtrate to any pretreatment. As a result, 391 g of methyl ethyl carbonate and 36 g of diethyl carbonate were obtained. The yields of methyl ethyl carbonate and diethyl carbonate based on the dimethyl carbonate fed as a starting material were 37.6% and 3.0%, respectively.

EXAMPLE 9

The same reaction as in Example 8 was carried out, except that the molar ratio between the ethyl alcohol and dimethyl carbonate used as starting materials was varied.

The resulting reaction mixtures were analyzed for composition by gas chromatography. The observed values obtained are shown in Table 4 in terms of molar ratio.

TABLE 4

| Molar ratio in starting materials (EtOH*$^1$/DMC*$^2$) | Reaction product molar ratio (DMC*$^2$/EMC*$^3$/DEC*$^4$) |
| --- | --- |
| 1.5 | 38/51/11 |
| 2.0 | 30/52/18 |
| 3.0 | 22/54/24 |
| 4.0 | 11/55/38 |
| 6.0 | 9/41/50 |
| 8.0 | 5/37/58 |
| 10.0 | 4/33/66 |

*$^1$: ethyl alcohol
*$^2$: dimethyl carbonate
*$^3$: ethyl methyl carbonate
*$^4$: diethyl carbonate

EXAMPLE 10

Into a stainless-steel autoclave having a capacity of 1,000 ml and equipped with a stirrer were introduced a solution prepared by mixing 345.8 g (7.5 mol) of ethyl alcohol and 225.3 g (2.5 mol) of dimethyl carbonate (molar ratio, 3:1) and 9.0 g (0.025 mol) of catalyst (1). Subsequently, the atmosphere in the reactor was replaced with nitrogen to regulate the nitrogen pressure inside the reactor to 2 kg/cm$^2$·G. The reactants were then reacted at 140° C. for 4 hours. The reaction pressure increased to 6.7 kg/cm$^2$·G at the time of initiation of the reaction at 140° C., thereafter increased gradually with progress of the reaction, and finally reached to 7.2 kg/cm$^2$·G at the time of completion of the reaction.

After completion of the reaction, the reaction mixture was analyzed. As a result, the reaction mixture was found to be composed of 87 g (2.7 mol) of methyl alcohol, 222 g (4.8 mol) of ethyl alcohol, 45 g (0.5 mol) of dimethyl carbonate, 136 g (1.3 mol) of ethyl methyl carbonate, and 81 g (0.7 mol) of diethyl carbonate and not to contain any other reaction product.

After this reaction mixture was cooled to room temperature, the catalyst was removed by filtration. The filtrate was distilled at ordinary pressure using a distilling column in which the number of theoretical plates was 20, without subjecting the filtrate to any pretreatment. As a result, 87 g of ethyl methyl carbonate and 32 g of diethyl carbonate were obtained. The yields of ethyl methyl carbonate and diethyl carbonate based on the dimethyl carbonate fed as a starting material were 33.4% and 10.8%, respectively.

EXAMPLE 11

The same procedure as in Example 10 was carried out, except that 7.4 g (0.033 mol) of catalyst (2) was used in place of catalyst (1). The resulting reaction mixture was composed of 93 g (2.9 mol) of methyl alcohol, 212 g (4.6 mol) of ethyl alcohol, 40.5 g (0.45 mol) of dimethyl carbonate, 125 g (1.2 mol) of ethyl methyl carbonate, and 99 g (0.85 mol) of diethyl carbonate, and did not contain any other reaction product.

EXAMPLE 12

The same procedure as in Example 10 was carried out, except that 5.0 g (0.033 mol) of catalyst (3) was used in place of catalyst (1). The resulting reaction mixture was composed of 90 g (2.8 mol) of methyl alcohol, 216 g (4.7 mol) of ethyl alcohol, 45 g (0.5 mol) of dimethyl carbonate, 130 g (1.25 mol) of ethyl methyl carbonate, and 89 g (0.75 mol) of diethyl carbonate, and did not contain any other reaction product.

COMPARATIVE EXAMPLE 2

The same procedure as in Example 10 was carried out, except that 2.5 g (0.033 mol) of catalyst (5) was used in place of catalyst (1). The resulting reaction mixture was composed of 10 g (0.3 mol) of methyl alcohol, 332 g (7.2 mol) of ethyl alcohol, 198 g (2.2 mol) of dimethyl carbonate, 31 g (0.3 mol) of ethyl methyl carbonate, and 1.2 g (0.01 mol) of diethyl carbonate, and did not contain any other reaction product.

EXAMPLE 13

A jacketed tubular reactor having an inner diameter of 54.9 mm and a length of 90 cm was packed with 127 ml (80 g) of catalyst (4) (cylindrical granules of a Co—Y compound oxide). A 1:1 (by mole) mixture of DMC and ethanol as starting materials was fed to the reactor with a constant delivery pump, and the pressure inside the reactor was regulated to 9 kg/cm$^2$G with nitrogen. Thereafter, the temperature of the contents was raised to 140° C. to conduct a continuous reaction while passing the reactants at LHSV's of from 1 to 3 and an average LHSV of 1.6. The cumulative amount of the reactants passed through the reactor during the period of 1,500 hours from initiation of the reaction was 300.6 kg (DMC, 199.0 kg; ethanol, 101.6 kg). The cumulative amounts of the EMC and DEC obtained and the cumulative amount of the remaining DMC were 98.9 kg, 25.4 kg, and 95.5 kg, respectively. As a result, the conversion of the DMC was 52%, the yield of EMC was 43%, and the yield of DEC was 9.7%. These values of yield were calculated based on the number of moles of the DMC used as a starting material. The yield of EMC per kg of the catalyst was 1,236 kg and that of DEC was 317 kg. Substantially no decrease in catalytic activity was observed.

EXAMPLE 14

The same reaction as in Example 13 was carried out at a nitrogen pressure of 9 kg/cm$^2$·G and a temperature of 140°

C., except that a 1:1.5 (by mole) mixture of DMC and DEC was fed as starting materials in place of DEC and ethanol, and that the continuous reaction was conducted while passing the reactants at LHSV's of from 1 to 5 and an average LHSV of 1.7. The cumulative amount of the reactants passed through the reactor during the period of 4,000 hours from initiation of the reaction was 866.0 kg (DMC, 291.5 kg; DEC, 574.1 kg). The cumulative amount of the EMC obtained and the cumulative amounts of the remaining DMC and DEC were 389.6 kg, 121.2 kg, and 355.0 kg, respectively. As a result, the conversion of the DMC was 58.4%, the conversion of the DEC was 38.2%, and the yield of EMC* was 47.0%. The yield of EMC, which was based on the number of moles of all carbonates fed as starting materials, was determined using the following equation. The yield of EMC per kg of the catalyst was 4,870 kg. Substantially no decrease in catalytic activity was observed.

*Note

Yield of EMC (%)=Yielded amount of EMC (mol)/{DMC feed amount (mol)+DEC feed amount (mol)}×100

While the invention has been described in detail and with reference to specific embodiments thereof, it will be apparent to one skilled in the art that various changes and modifications can be made therein without departing from the spirit and scope thereof.

What is claimed is:

1. A process for producing an unsymmetrical chain carbonic acid ester which comprises reacting a first symmetrical chain carbonic acid ester with a second symmetrical chain carbonic acid ester or a monohydric alcohol in the presence of a catalyst comprising as an active catalyst component an oxide of at least one element selected from the Group IIIB elements of the periodic table.

2. The process as claimed in claim 1, wherein said first symmetrical chain carbonic acid ester is reacted with said second symmetrical chain carbonic acid ester by disproportionation.

3. The process as claimed in claim 1, wherein said first symmetrical chain carbonic acid ester is reacted with said monohydric alcohol by transesterification.

4. The process as claimed in claim 1, wherein the at least one Group IIIB element is at least one of samarium and yttrium.

5. The process as claimed in claim 2, wherein the first and second symmetrical chain carbonic acid esters subjected to disproportionation are dimethyl carbonate and diethyl carbonate and the ester to be produced is ethyl methyl carbonate.

6. The process for producing an unsymmetrical chain carbonic acid ester as claimed in claim 3, wherein the carbonic acid ester subjected to transesterification is dimethyl carbonate and the monohydric alcohol is ethyl alcohol.

7. The process as claimed in claim 5, wherein the reaction is conducted at a temperature of from 0° to 300° C. and a pressure of from 0.1 to 100 kg/cm²·G.

8. The process as claimed in claim 1, wherein the molar ratio of the alcohol to the carbonic acid ester is from 0.5 to 5.

9. The process as claimed in claim 6, wherein the reaction is conducted at a temperature of from 0° to 300° C. and a pressure of from 0 to 60 kg/cm²·G.

10. The process as claimed in claim 1, wherein the oxide as a catalyst component is porous and has a specific surface area of from 5 to 500 m²/g.

11. A process for producing an unsymmetrical chain carbonic acid ester which comprises reacting a first symmetrical chain carbonic acid ester with a second symmetrical chain carbonic acid ester or a monohydric alcohol in the presence of a catalyst comprising as an active catalyst component, an oxide of at least one element selected from the Group IIIB elements of the periodic table, wherein the catalyst comprises yttrium oxide and cobalt oxide.

12. The process as claimed in claim 4, wherein the catalyst comprises samarium oxide and cobalt oxide.

13. The process as claimed in claim 1, wherein said first and second symmetrical chain carbonic acid esters each comprise linear alkyl groups of from one to six carbon atoms, and the monohydric alcohol is selected from aliphatic alcohol having one to six carbon atoms.

14. The process as claimed in claim 1, wherein the symmetrical chain carbonic acid esters are selected from dimethyl carbonate, diethyl carbonate, dipropyl carbonate, dibutyl carbonate and dicyclohexyl carbonate, and the monohydric alcohol is selected from methyl alcohol, ethyl alcohol, n-propyl alcohol, isopropyl alcohol, n-butyl alcohol, isobutyl alcohol, t-butyl alcohol, pentyl alcohol, hexyl alcohol, octyl alcohol, 2-ethylhexyl alcohol, decyl alcohol, dodecyl alcohol, tetra-decyl alcohol, hexadecyl alcohol, octadecyl alcohol and cyclohexyl alcohol.

15. The process as claimed in claim 1, wherein the unsymmetrical chain carbonic acid ester produced is one of ethyl methyl carbonate, methyl propyl carbonate, ethyl propyl carbonate, butyl methyl carbonate, butyl ethyl carbonate and butyl propyl carbonate.

16. The process as claimed in claim 4, wherein the catalyst additionally includes cobalt compound.

17. The process as claimed in claim 10, wherein the oxide has a specific surface area of from 10 to 300 m²/g.

18. The process as claimed in claim 7, wherein the reaction is conducted at a temperature of from 50° to 200° C. and a pressure of from 0 to 50 kg/cm²·G.

19. The process as claimed in claim 9, wherein the reaction is conducted at a temperature of from 50° to 200° C. and a pressure of from 0 to 30 kg/cm²·G.

20. The process as claimed in claim 1, wherein the monohydric alcohol is selected from primary and secondary alcohols.

* * * * *